United States Patent [19]

Patel et al.

[11] 4,055,187

[45] Oct. 25, 1977

[54] CATHETER WITH IMPROVED BALLOON ASSEMBLY

[75] Inventors: Bhupendra C. Patel, Elgin; William J. Binard, Cary; Daniel M. McWhorter, Arlington Heights, all of Ill.

[73] Assignee: The Kendall Company, Boston, Mass.

[21] Appl. No.: 711,948

[22] Filed: Aug. 5, 1976

[51] Int. Cl.² ............................................. A61M 25/00
[52] U.S. Cl. ................................. 128/349 B; 128/246
[58] Field of Search .............. 128/348, 349 R, 349 B, 128/349 BV, 350 R, 351, 246, 344

[56] References Cited

U.S. PATENT DOCUMENTS

| | | | |
|---|---|---|---|
| 3,173,418 | 3/1965 | Baran | 128/349 B |
| 3,812,860 | 5/1974 | Gilbert et al. | 128/349 B |
| 3,832,253 | 8/1974 | Palma et al. | 128/349 B X |
| 3,884,242 | 5/1975 | Bazell et al. | 128/349 B X |
| 3,926,705 | 12/1975 | Todd | 128/349 B X |

*Primary Examiner*—Dalton L. Truluck
*Attorney, Agent, or Firm*—Powell L. Sprunger

[57] ABSTRACT

A catheter comprising, an elongated shaft having a main lumen and an inflation lumen extending along a wall of the shaft. The catheter has a balloon assembly in which an expansible sleeve is joined at spaced zones to an underlying sleeve or tube of a material providing compatible bonding characteristics with the sleeve to facilitate attachment of the balloon onto the shaft.

11 Claims, 11 Drawing Figures

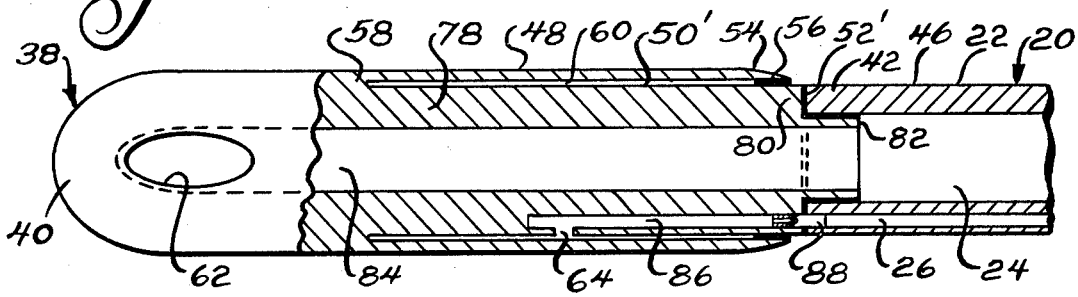
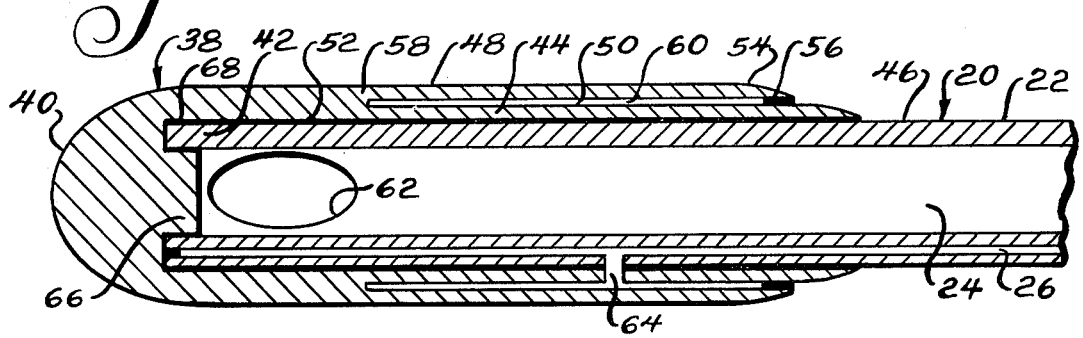
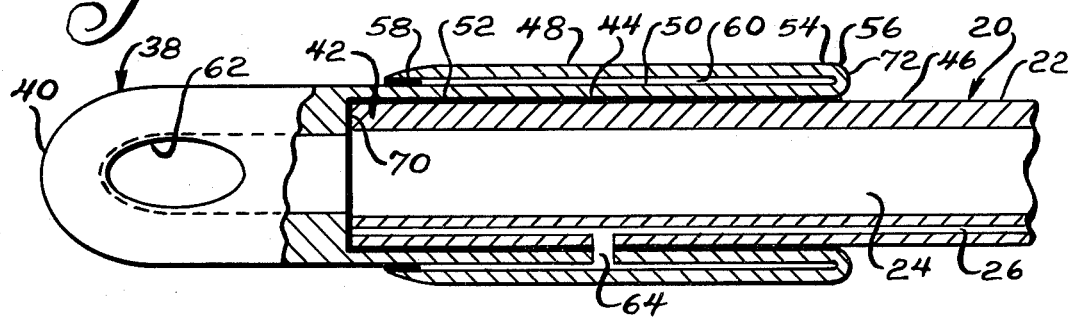
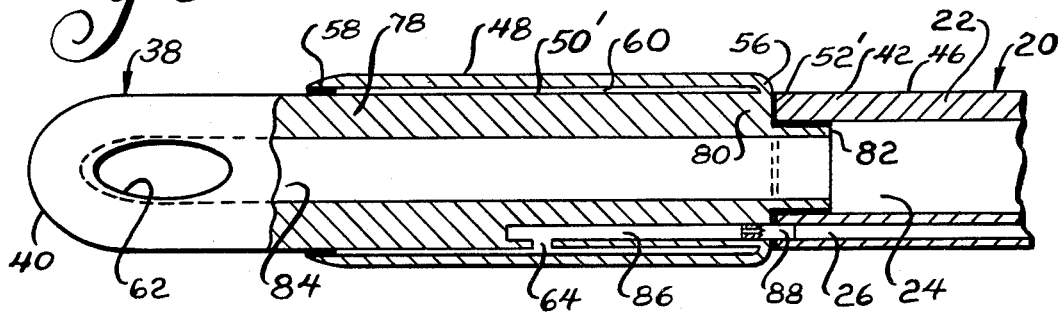

CATHETER WITH IMPROVED BALLOON ASSEMBLY

BACKGROUND OF THE INVENTION

The present invention relates to catheters, and more particularly to balloon assemblies for such catheters.

In the past, a various assortment of catheters, such as Foley catheters and endotracheal tubes, have been proposed for use in patients. In the case of urinary catheters, a conventional Foley catheter is normally constructed having a shaft defining a drainage lumen extending from a drainage eye adjacent a distal end of the shaft and an inflation lumen in the wall of the shaft, and having an expansible balloon overlying a distal portion of the shaft and defining a cavity communicating with the inflation lumen. In use, the distal end of the catheter is passed through the urethra until the drainage eye and balloon are located in the patient's bladder, and the balloon is inflated in the bladder to retain the catheter in the patient with a proximal end of the catheter located outside the patient's body. During catheterization, urine passes from the bladder through the drainage eye and lumen, and from the catheter through a drainage tube to a bag for collection therein.

A great majority of Foley catheters have been made from latex rubber through dipping techniques known to the art. However, a number of problems have been encountered with conventional latex catheters, such as difficulties in manufacture and delamination of the catheter sidewalls causing blockage in the inflation lumen. Accordingly, there has been a desire to construct catheters from materials which display superior properties both from the view of improved performance during use and permitting simplified manufacture to reduce cost. For example, it is preferred that the catheter shaft be made from a material which can be extruded in order to facilitate the manufacturing process and eliminate the delamination problems associated with dipped latex catheters. Additionally, the materials of the catheter shaft must be compatible with the patient's body to prevent deleterious results during use. The shaft, although flexible, should also have sufficient rigidity to permit placement of the catheter and prevent collapse of the shaft side walls. The balloon, of course, should be flexible and elastic to permit inflation in the patient's bladder, and preferably has a sufficient memory to assume its initial deflated configuration against the catheter shaft while being removed from the patient. It is desirable that the balloon may be formed by extrusion or molding techniques, or it may be preferred to mold the balloon and catheter tip as a single unit.

Unfortunately, many of the materials which display excellent properties when used for the catheter shaft are not suitable as a balloon, and vice versa. Hence, in many cases it is necessary to use dissimilar materials for the balloon and shaft which has created serious difficulties in joining the balloon and shaft together. Although it is often relatively simple to obtain a satisfactory bond between the balloon and shaft when the same material is used for both, known bonding techniques such as adhesive or heat sealing often do not provide sufficient strength between the balloon and shaft when dissimilar materials are used. For example, porous polytetrafluoroethylene provides an excellent candidate for the catheter shaft, but has been found unsatisfactory as the catheter balloon. Accordingly, attempts have been made to bond balloons made of suitable materials, such as silicone and latex, to such a shaft, and satisfactory bonds are only obtained with extreme difficulty which unduly complicates manufacture of the catheters.

SUMMARY OF THE INVENTION

A principal feature of the present invention is the provision of a catheter having an improved balloon assembly for attachment to a catheter shaft.

The catheter of the present invention comprises, an elongated shaft having a main lumen and an inflation lumen extending along a wall of the shaft. The catheter has a balloon assembly having an expansible sleeve which may be made of a material dissimilar to the material of the catheter shaft. An inner sleeve or tube, which is made of a material similar to that of the expansible sleeve, is attached to a distal end of the catheter shaft in a manner obtaining a secure bond, and the expansible sleeve is joined to the inner sleeve or tube at spaced proximal and distal zones extending circumferentially around the balloon assembly. In one embodiment, the expansible sleeve may be integral with the inner sleeve or tube, and, in alternative embodiments, the expansible sleeve may be separate from the inner sleeve or tube.

A feature of the present invention is that the inner sleeve or tube is secured to the shaft in a manner obtaining a firm bond.

Another feature of the present is that the expansible sleeve may be readily joined to the inner sleeve or tube in a manner obtaining a firm bond.

Thus, a further feature of the present invention is that the catheter of the present invention may be made in a simplified manner while obtaining a firm bond of the expansible sleeve onto the catheter shaft.

Another feature of the present invention is that dissimilar materials may be used for the catheter shaft and expansible sleeve resulting in a catheter having improved characteristics.

Still another feature of the present invention is that the catheter of the present invention may be made according to simplified manufacturing techniques thus reducing the cost of the catheter to the consumer.

Further features will becomes more fully apparent in the following description of the embodiments of this invention and from the appended claims.

DESCRIPTION OF THE DRAWINGS

In the drawings:

FIG. 5 is a fragmentary view, taken partly in section, of another embodiment of the catheter of the present invention;

FIG. 6 is a fragmentary sectional view of another embodiment of the catheter of the present invention;

FIG. 7 is a fragmentary view, taken partly in section, of another embodiment of the catheter of the present invention;

FIG. 8 is a fragmentary view, taken partly in section, of another embodiment of the catheter of the present invention;

DESCRIPTION OF THE PREFERRED EMBODIMENTS

Figure 1:
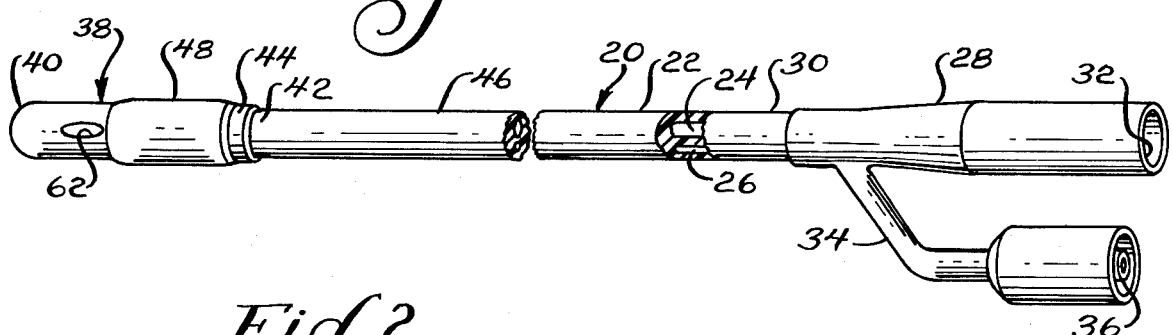
FIG. 1 is a fragmentary elevational view taken partly in section, of the catheter of the present invention.
Figure 2:
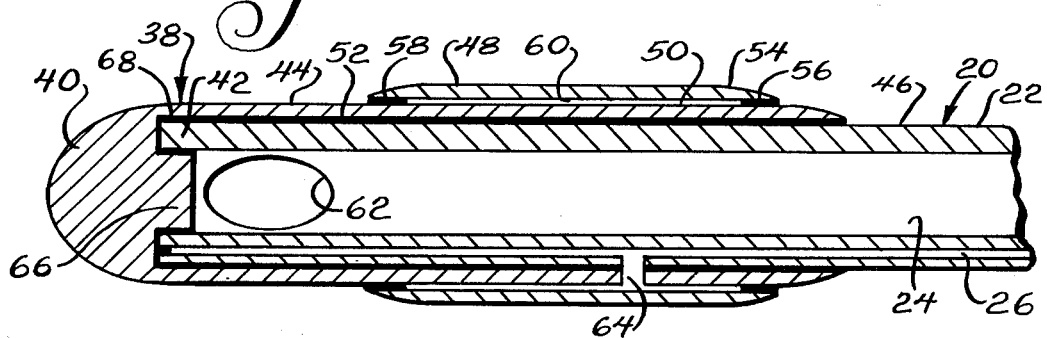
FIG. 2 is a fragmentary sectional view of the catheter of FIG. 1.

Referring now to FIGS. 1 and 2, there is shown a urinary catheter generally designated 20 for draining urine from the bladder of a patient. Although the present invention will be described in connection with a urinary catheter, it will be understood that the principals of the present invention are equally applicable to other suitable catheters, such as endotracheal tubes. The catheter 20 has an elongated shaft 22 which in a preferred form is made from a material which can be extruded. The shaft 22 has a main or drainage lumen 24 extending through the shaft and an inflation lumen 26 extending through a wall of the shaft. The catheter 20 has a connector 28 secured to a proximal end 30 of the shaft 22, with the connector 28 having a channel 32 communicating with the drainage lumen 24 of the shaft 22. The connector 28 also has a side arm 34 defining a continuation of the inflation lumen 26 which communicates with valve means 36 at an outer end of the side arm 34.

The catheter 20 also has a balloon assembly generally designated 38 comprising a rounded tip 40 secured to a distal end 42 of the shaft 22, a first inner sleeve 44 secured to an outer surface 46 of the shaft 22 adjacent the distal end thereof, and an outer second expansible sleeve 48 secured to an outer surface 50 of the first sleeve 44. The catheter shaft 22 and balloon assembly 38 may be made from dissimilar materials while still obtaining an excellent bond between the various members in accordance with the present invention. Thus, as shown in FIG. 2, the first sleeve 44 is bonded to the outer surface 46 of the shaft 22 throughout a substantial region between their adjoining surfaces by suitable adhesive 2, such as solvent or epoxy types. Additionally, the inner diameter of the first sleeve 44, which is made of a flexible and elastic material, may be less than the outer diameter of the shaft 22, in order to also obtain a mechanical bond between the first sleeve 44 and shaft 22. The adhesive 52 joining the inner sleeve 44 to the shaft 22 thus extends throughout a sufficient region to obtain a suitable bond between the sleeve 44 and shaft 22, which could not normally be obtained if the balloon is secured directly to the shaft in limited reas, particularly if dissimilar materials are used for the balloon and shaft.

As shown in FIG. 2, a proximal end 54 of the second sleeve 48 is secured to the outer surface 50 of the first sleeve 44 in a first proximal zone 56 extending circumferentially around the shaft and balloon assembly, and the separate second sleeve 48 is also secured to the outer surface 50 of the first sleeve 44 in a second distal zone 58 extending circumferentially around the shaft and balloon assembly. Since the first and second sleeves 44 and 48, respectively, are made of the same or similar material, the bonds in the zones 56 and 58 may be readily obtained through use of known adhesives or by sealing, such as heat or impulse sealing, in the zones. The first and second sleeves 44 and 48, along with the first and second zones 56 and 58, define a fluid receiving cavity 60 intermediate the first and second sleeves 44 and 48.

As shown, the catheter has a drainage eye 62 extending through the shaft 22 and first sleeve 44, such that the eye 62 communicates between the outside of the balloon assembly 38 and the drainage lumen 24. Also, the catheter has an aperture or opening means 64 extending through the outer wall portion of the shaft 22 and through the first sleeve 44, such that the aperture 64 communicates between the inflation lumen 26 and the cavity 60. In the particular embodiment shown, the tip 40 has a plug 66 extending from a proximal end of the tip 40 and defining an annular groove 68, with the plug 66 being received in the drainage lumen 24 of the shaft 22 and with the distal end 42 of the shaft 22 being received in the groove 68.

The shaft 22 may be made of any suitable material which is somewhat flexible while being sufficiently rigid to permit placement of the shaft through the urethra of the patient and prevent collapse of the shaft side walls. Also, the material of the shaft 22 must be compatible with the patient's body to prevent deleterious results during use. In a suitable form, the shaft 22 may be made from porous polytetrafluoroethylene, polyvinylchloride, urethane, polyethylene, or suitable thermosplastic material. In a preferred form, the outer sleeve 48 is made from a material which is flexible and elastic to permit inflation in the patient's bladder, and exhibits sufficient memory such that the outer sleeve assumes a configuration in its deflated state against the shaft to permit removal of the catheter from the patient. Suitable materials for the outer sleeve 48 are silicone, latex, or other elastic material.

As previously indicated, in the absence of the first inner sleeve 44, it would be extremely difficult to obtain a suitable bond between such materials for the outer sleeve 48 in the limited regions the balloon is normally attached to the catheter shaft. Even if a suitable bond could be obtained between the dissimilar materials, the manufacturing procedures are rendered extremely time consuming and difficult, thus making the cost of such a catheter prohibitive. In accordance with the present invention, the inner sleeve 44 is bonded through a substantial region to the outer surface of the shaft 22 in order to obtain a firm bond between the first sleeve 44 and the shaft 22, after which the outer sleeve 48 may be bonded to the sleeve 44 in a simplified and firm manner, since the inner and outer sleeves 44 and 48 may be made from the same or similar material.

In use, the distal end of the catheter is passed through the urethra until the drainage eye 62 and expansible sleeve 48 are positioned in the patient's bladder after which the sleeve 48 is inflated through the valve means 36. Next, a drainage tube (not shown) is attached in the connector 28 of the catheter 20 with a lumen in the drainage tube communicating with the channel 32 of the connector. During catheterization, urine passes through the drainage eye 62 and the drainage lumen 24 of the shaft 22 to the drainage tube, after which the urine passes from the drainage tube into a bag (not shown) for collection therein.

Figure 3:
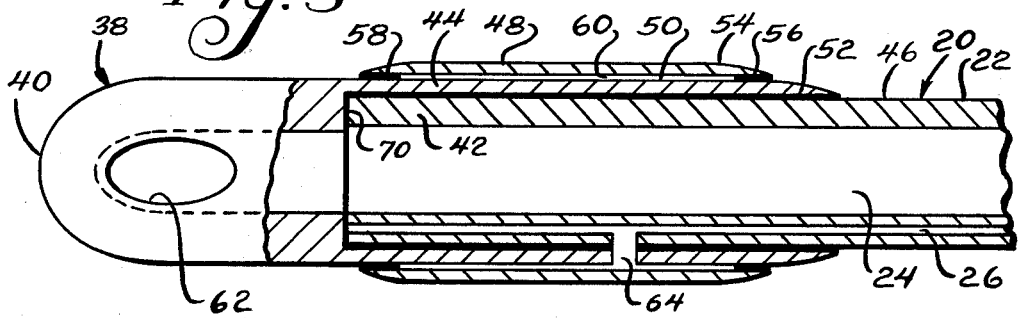
FIG. 3 is a fragmentary view, taken partly in section, of another embodiment of the catheter of the present invention.

Another embodiment of the present invention is illustrated in FIG. 3, in which like reference numerals designate like parts. In this embodiment, the balloon assembly 38 also has a first sleeve 44 extending proximally from the tip 40, with the sleeve 44 being secured by suitable adhesive 52 to the outer surface 46 of the shaft 22, and an outer expansible sleeve 48 is secured to the sleeve 44 in spaced proximal and distal zones 56 and 58. However, in this embodiment, the tip 40 has an annular shoulder 70 abutting and being secured to the distal end of the shaft 22 by adhesive.

Another embodiment of the present invention is illustrated in FIG. 6, in which like reference numerals designate like parts. In this embodiment, the outer sleeve 48 is integral with the remainder of the balloon assembly 38, such that the first and second sleeves 44 and 48 are of one-piece construction in the distal zone 58 where they are joined together. Thus, the outer sleeve 48 is positioned over the outer surface 50 of the inner sleeve 44, and the first and second sleeves 44 and 48 are bonded together by suitable means in the proximal zone 56, in order to define the cavity 60 between the sleeves. In a preferred form, the balloon assembly may be molded from a suitable material, such as silicone, as a single unit.

Another embodiment of the present invention is illustrated in FIG. 7, in which like reference numerals designate like parts. In this embodiment, the outer sleeve 48 is also integral with the remainder of the balloon assembly 38, with the outer sleeve 48 extending from a proximal end of the first sleeve 44. Thus, the first and second sleeves 44 and 48 are of one-piece construction at their proximal ends, and the outer sleeve 48 is folded back over the inner sleeve 44 along a fold line 72 where the sleeves are joined together in the proximal zone 56 by the fold. The distal end of the outer sleeve 48 is bonded to the outer surface of the inner sleeve 44 or the tip, as desired. In a preferred form, the balloon assembly 38 may be molded as a single unit from a suitable material, such as silicone, after which the inner sleeve 44 is secured to the outer surface of the shaft 22, and the outer sleeve 48 is folded back and secured in place.

Figure 9:
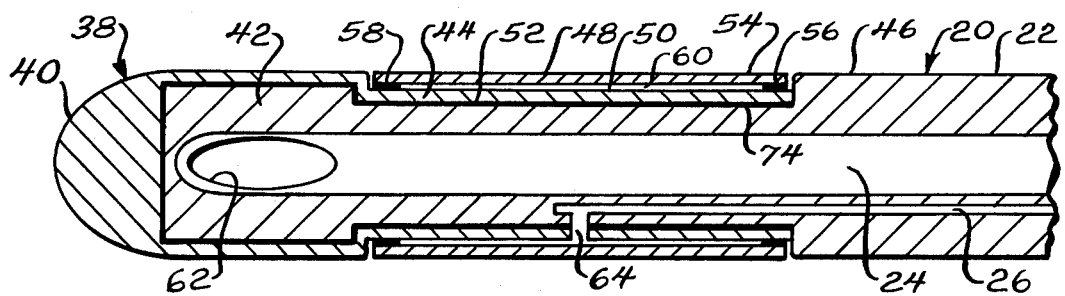
FIG. 9 is a fragmentary sectional view of another embodiment of the catheter of the present invention.

Another embodiment of the present invention is illustrated in FIG. 9, in which like reference numerals designate like parts. In this embodiment, the shaft 22 has an annular recess 74 in its outer surface 46 to receive the proximal end of the inner sleeve 44. In a preferred form, the length of the recess 74 is sufficient to receive the inner sleeve 44 intermediate the proximal and distal bonding zones 56 and 58, as shown, and the recess 74 also has a sufficient depth to receive the inner and outer sleeves 44 and 48 such that the outer sleeve 48 assumes a flush configuration with the outer surface 46 of the shaft 22. Thus, a relatively smooth surface is defined between the balloon assembly 38 and the outer surface 46 of the shaft 22. The second sleeve 48 is secured or bonded to the inner sleeve 44 in the first and second zones 56 and 58 in a manner as previously described.

Figure 10:
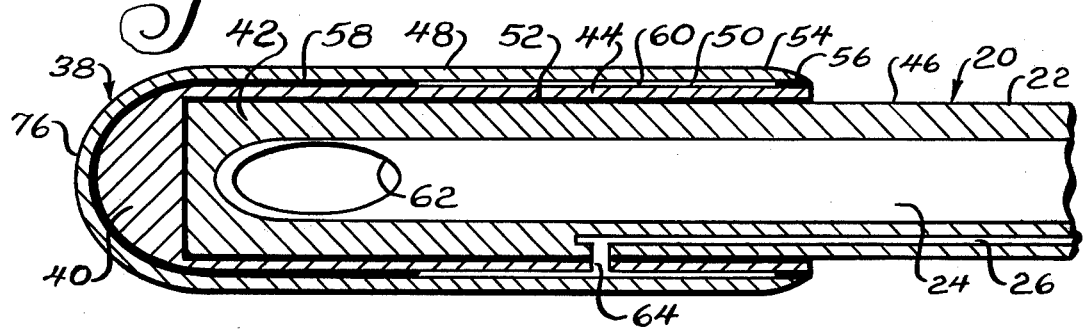
FIG. 10 is a fragmentary sectional view of another embodiment of the catheter of the present invention.

Another embodiment of the present invention is illustrated in FIG. 10, in which like reference numerals designate like parts. In this embodiment, the second sleeve 48 includes a distal portion 76 extending around the tip 40, and, if desired, the distal bonding zone 58 may extend completely around the tip bonding the tip 40 and distal sleeve portion 76, as shown. The proximal end of the outer sleeve 48 is bonded to the outer surface of the inner sleeve 44 in the proximal zone 56, as previously described, in order to define the cavity 60 which extends between the first and second zones 56 and 58.

Figure 4:
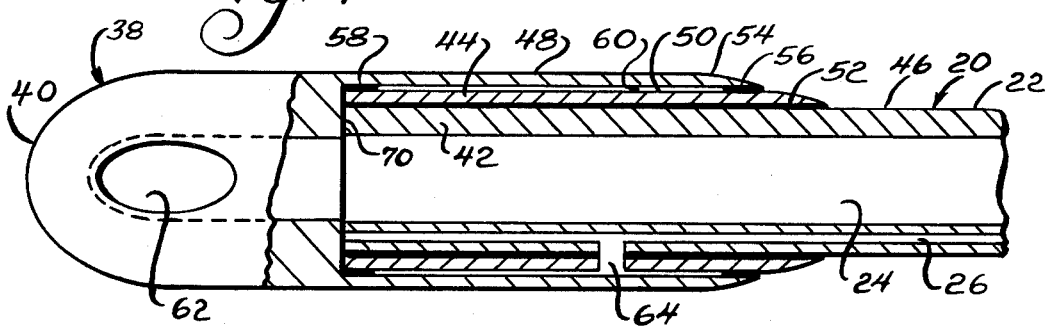
FIG. 4 is a fragmentary view, taken partly in section; of another embodiment of the catheter of the present invention.

Another embodiment of the present invention is illustrated in FIG. 4, in which like reference numerals designate like parts. In this embodiment, the second outer sleeve 48 extends proximally from the tip 40, and the first inner sleeve 44 comprises a separate sleeve located intermediate the outer sleeve 48 and the outer surface 46 of the shaft 22, although, if desired, the inner sleeve 44 may be of one-piece construction with the proximal end of the outer sleeve 48. The inner sleeve 44 is secured to the outer surface 46 of the catheter shaft 22 by suitable means, such as by adhesive 52, and the outer sleeve 48 is bonded to the outer surface 50 of the inner sleeve 44 in the proximal and distal zones 56 and 58, in a manner as previously described.

Figure 11:
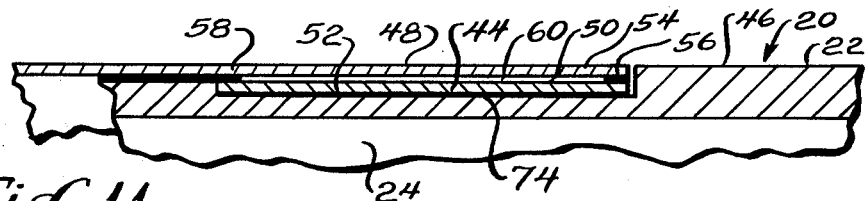
FIG. 11 is a fragmentary sectional view of another embodiment of the catheter of the present invention.

Another embodiment of the present invention is illustrated in FIG. 11, in which like reference numerals designate like parts. In this embodiment the shaft 22 has an annular recess 74 in its outer surface and being of sufficient length to receive the inner sleeve 44, as shown. Also, the recess 74 has a sufficient depth such that the outer sleeve 48 assumes a flush configuration with the outer surface 46 of the shaft 22. The inner sleeve 44 is secured to the shaft by suitable means, such as adhesive 52, while the outer sleeve 48 is secured to the inner sleeve in the spaced proximal and distal zones 56 and 58, as previously described.

Another embodiment of the present invention is illustrated in FIG. 5, in which like reference numerals designate like parts. In this embodiment, the balloon assembly 38 has a tube 78 extending proximally from the tip 40, and the tube 78 has a proximal end 80 secured to the distal end 42 of the catheter shaft 22 by adhesive 52'. In a preferred form, the tube 78 has an annular tongue 82 adjacent an inner surface of the tube and extending from the proximal end 80 of the tube, with the tongue 82 being received in the distal end of the shaft drainage lumen 24, as shown. The outer diameter of the tongue 82 is approximately equal to the inside diameter of the drainage lumen 24, and the proximal end 80 and tongue 82 of the tube 78 are bonded to the distal end 42 of the shaft 22 by the adhesive 52'.

In this embodiment, the tube 78 has a lumen 84 communicating between the drainage lumen 24 of the shaft 22 and the drainage eye 62. Also, the tube 78 has a channel 86 extending through a side wall of the tube 78 and communicating between the aperture 64 and the inflation lumen 26 of the shaft. In a preferred form, the catheter has a tubular section 88 extending between the channel 86 of the tube 78 and the inflation lumen 26 of the shaft 22 in order to facilitate establishment of communication between the channel 86 and inflation lumen 26. Also, the balloon assembly 38 has an integral outer sleeve 48 which extends proximally from the tip 40 and which is of one-piece construction with the tube and tip in the distal zone 58. As shown, the proximal end 54 of the outer sleeve 48 is bonded by suitable means to the outer surface 50' of the tube 78 in the proximal zone 56. In an alternative form, the outer expansible sleeve 48 may be made from a separate piece, and may be bonded to the outer surface of the tube 78 in the proximal and distal zones 56 and 58. The catheter of FIG. 5 operates in a manner as previously described, with the sleeve 48 being inflated by passage of inflation fluid through the inflation lumen 26, the tubular section 88, the channel 86, and the aperture 64 into the cavity 60 located intermediate the outer sleeve 48 and the tube 78.

Another embodiment of the present invention is illustrated in FIG. 8, in which like reference numerals designate like parts. In this embodiment, the outer expansible sleeve 48 is also integral with the tube 78, and extends from the proximal end 80 of the tube 78, as shown. Thus, the outer sleeve 48 is of one-piece construction with the tube 78 in the proximal zone 56, and the sleeve 48 is folded back and bonded to the outer surface 50' of the tube 78 in the distal zone 58, in order to define the cavity 60 intermediate the outer sleeve 48 and the tube 78. In other respects, the catheter of FIG. 8 is similar to the catheter previously described in connection with FIG. 5.

The foregoing detailed description is given for clearness of understanding only, and no unnecessary limitations should be understood therefrom, as modifications will be obvious to those skilled in the art.

We claim:

1. A catheter, comprising:
an elongated shaft having a main lumen and an inflation lumen extending along a wall of the shaft; and
a balloon assembly comprising a tip secured to a distal end of the shaft, a first sleeve extending proximally from the tip and being bonded to an outer surface of the shaft adjacent the distal end thereof, said first sleeve being of one-piece construction with said tip, an expansible second sleeve overlying and being joined to the first sleeve at a first proximal zone extending circumferentially around the assembly and being joined to the assembly at a second zone extending circumferentially around the assembly at a location spaced distally from said proximal zone to define a fluid receiving cavity intermediate the first and second sleeves, and opening communicating between the main lumen of the shaft and an outer surface of the assembly at a location distal said cavity, and opening means communicating between the cavity and the inflation lumen for inflation of the second sleeve.

2. The catheter of claim 1 wherein the first and second sleeves are separate, and in which the second sleeve is bonded to an outer surface of the first sleeve.

3. The catheter of claim 1 wherein said opening extends through said tip at a location distal the first sleeve.

4. The catheter of claim 2 wherein said tip has an annular shoulder abutting against the distal end of the shaft.

5. The catheter of claim 1 wherein said opening extends through the first sleeve, and in which the shaft has an aperture communicating with the main lumen and in alignment with said opening.

6. The catheter of claim 5 in which the tip includes a plug at its proximal end defining an annular groove, said plug being received in the main lumen of the shaft, and the distal end of the shaft being received in said groove.

7. The catheter of claim 1 wherein said shaft includes an aperture at an outer surface of the shaft communicating with the inflation lumen, and in which the opening means comprises an aperture in the first sleeve communicating between the shaft aperture and said cavity.

8. The catheter of claim 1 wherein said shaft includes an annular recess in an outer surface of the shaft, with said recess having a sufficient length to receive said first sleeve intermediate said first and second zones.

9. The catheter of claim 1 wherein said first and second sleeves are of one-piece construction in said distal zone, said second sleeve extends proximally from said distal zone, and in which said second sleeve is bonded to the first sleeve in said proximal zone.

10. A catheter, comprising:
an elongated shaft having a main lumen and an inflation lumen extending along a wall of the shaft; and
a balloon assembly comprising a tip secured to a distal end of the shaft, a first sleeve extending proximally from the tip and being secured to an outer surface of the shaft adjacent the distal end thereof, an expansible second sleeve overlying and being joined to the first sleeve at a first proximal zone extending circumferentially around the assembly and being joined to the assembly at a second zone extending circumferentially around the assembly at a location spaced distally from said proximal zone to define a fluid receiving cavity intermediate the first and second sleeves, an opening communicating between the main lumen of the shaft and an outer surface of the assembly at a location distal said cavity, and opening means communicating between the cavity and the inflation lumen for inflation of the second sleeve, said second sleeve extending from said distal zone around an outer surface of the tip, with said opening extending through the second sleeve.

11. A catheter comprising:
an elongated shaft having a main lumen and an inflation lumen extending along a wall of the shaft; and
a balloon assembly comprising a tip secured to a distal end of the shaft, a first sleeve extending proximally from the tip and being secured to an outer surface of the shaft adjacent the distal end thereof, an expansible second sleeve overlying and being joined to the first sleeve at a first proximal zone extending circumferentially around the assembly and being joined to the assembly at a second zone extending circumferentially around the assembly at a location spaced distally from said proximal zone to define a fluid receiving cavity intermediate the first and second sleeves, an opening communicating between the main lumen of the shaft and an outer surface of the assembly at a location distal said cavity, and opening means communicating between the cavity and the inflation lumen for inflation of the second sleeve, said first and second sleeves being of one-piece construction in said proximal zone, said second sleeve being folded back over the first sleeve along a fold line at the proximal ends of the first and second sleeves, and said second sleeve being bonded to an outer surface of the assembly in said distal zone.

* * * * *